United States Patent [19]

Hogan

[11] 4,439,191

[45] Mar. 27, 1984

[54] OSTOMY BAG COVER

[76] Inventor: Elizabeth R. Hogan, 309 Dartmore P.O. Box 194, Whitmore Lake, Mich. 48189

[21] Appl. No.: 397,994

[22] Filed: Jul. 14, 1982

[51] Int. Cl.$^3$ ................................................ A61F 5/44
[52] U.S. Cl. ...................................... 604/332; 604/337
[58] Field of Search ......................... 604/277, 332–345, 604/327

[56] References Cited

U.S. PATENT DOCUMENTS

| Re. 29,453 | 10/1977 | Weddle | 604/344 |
| 2,662,525 | 12/1953 | Priebe | 604/343 |
| 3,039,464 | 6/1962 | Galindo | 128/283 |
| 3,089,493 | 5/1963 | Galindo | 128/283 |
| 3,385,298 | 5/1968 | Fenton | 604/332 |
| 3,802,418 | 4/1974 | Clayton | 128/2 F |
| 3,897,785 | 8/1975 | Barto | 604/327 |
| 4,173,979 | 11/1979 | Odis | 128/295 |
| 4,185,630 | 1/1980 | Neumeier et al. | 604/344 |

Primary Examiner—C. Fred Rosenbaum
Assistant Examiner—J. L. Kruter
Attorney, Agent, or Firm—Basile, Weintraub & Hanlon

[57] ABSTRACT

An ostomy bag cover for an ostomy bag of the type having an inlet, a connecting member for connecting the inlet in communication with a stoma on a wearer's body and a closeable outlet at the bottom of the ostomy bag for emptying the contents therefrom. The cover is in the form of a hollow body and includes a first aperture formed therein adapted to be disposed in registry with the inlet of the ostomy bag and to receive the connecting member therethrough. A second aperture is formed in the bottom of the hollow body between spaced side portions thereof and is adapted to be disposed in proximity with the outlet of the ostomy bag. A releasable fastener is mounted on the space sides for releaseably closing the second aperture in the hollow body.

6 Claims, 4 Drawing Figures

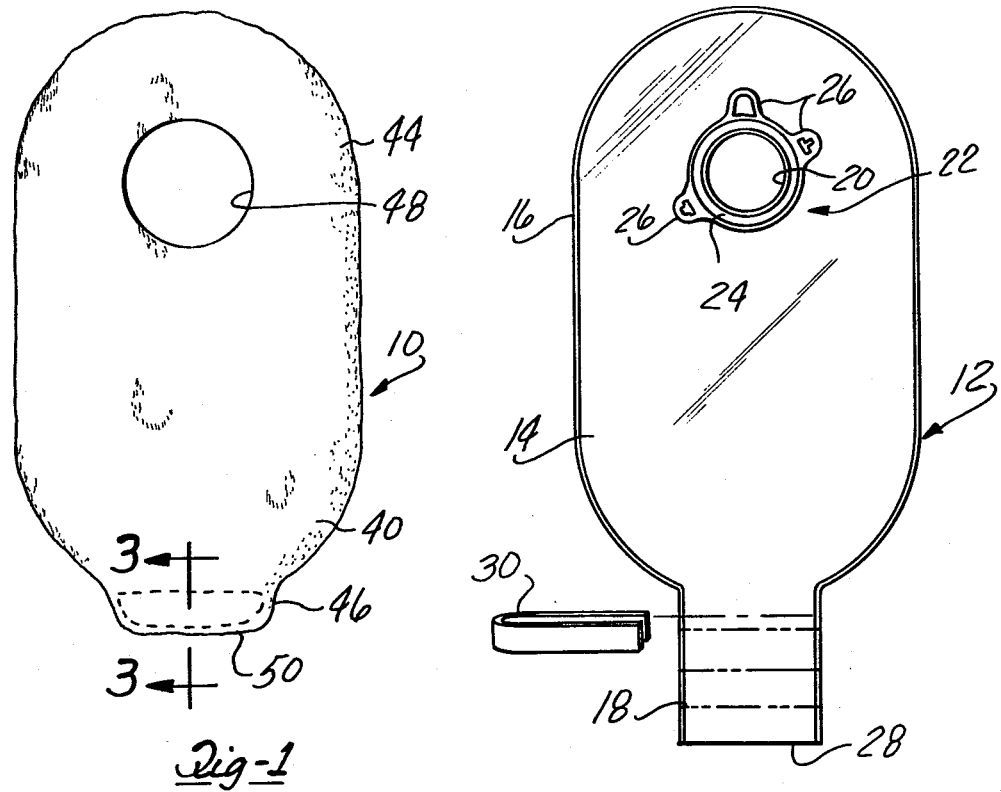
Fig-1
Fig-2
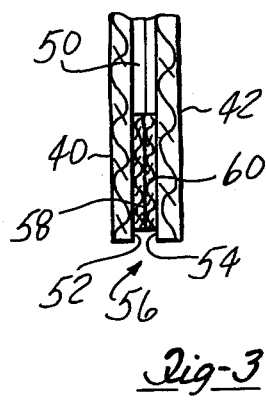
Fig-3
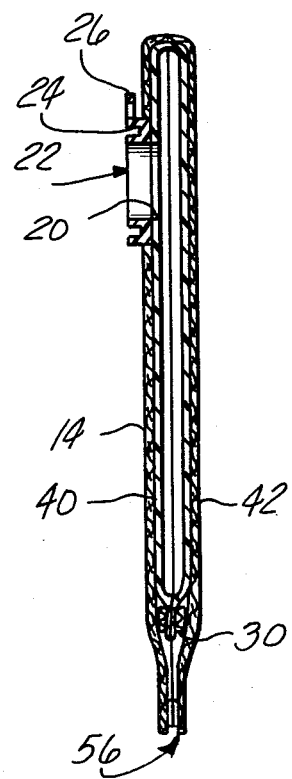
Fig-4

OSTOMY BAG COVER

BACKGROUND OF THE INVENTION

I. Field of the Invention

This invention relates, in general, to ostomy bags and, more specifically, to covers for ostomy bags.

II. Description of the Prior Art

In persons having intestinal problems which render all or a portion of the intestines inoperative due to disease or other pathological conditions or temporarily inoperative due to inflamation or surgery, a surgical procedure known as an ostomy is performed in which a passageway or stoma is made through the skin typically through the abdominal wall. A portion of the intestine is re-routed and surgically connected to the stoma such that waste material can exit the body.

The term "ostomy" covers all types of surgical procedures wherein a passageway is formed through the skin and a portion of the intestine connected thereto. When a portion of the large intestine or colon is connected to the stoma or passageway, the surgical procedure is referred to as a "colostomy". When the small intestine is involved, the surgical procedure is known as a "ileostomy". Both types of procedures require an ostomy bag which is affixed to or worn on the body and is in communication with the stoma to collect waste material exiting therethrough. A wide variety of ostomy bags and methods for attaching them to the body have been previously devised.

A common type of ostomy bag which has found widespread use is formed of a plastic material and has an aperture located on one side in which a means for attaching the ostomy bag to the body is mounted so as to dispose the interior of the bag in communication with the stoma for receiving waste material exiting the body through the stoma. The bottom end of the bag is in the form of a narrow throat and has a slot formed therein. The throat is typically folded up and secured in place by a removable fastener to sealingly close the bottom of the bag so as to retain the waste material therein and, yet, enable the bag to be opened for emptying the contents therefrom.

Although such ostomy bags effectively collect waste material, they are not without certain disadvantages. Previously devised ostomy bags are typically formed of a transparent or semi-transparent material which renders the collected body waste material in the bag somewhat visible. Furthermore, as ostomy bags are typically formed of a plastic material, they have a tendency to stick to the body of the wearer and cause discomfort and/or skin irritation.

Covers have been previously devised which surround and enclose an ostomy bag. However, such previously devised covers are sealed at the bottom such that the ostomy bag cannot be emptied without completely removing the bag and the cover from the body of the wearer. This is a time consuming and unpleasant task at best and, further, could cause irritation to the skin surrounding the stoma due to frequent removal and reattachment of the ostomy bag.

Other ostomy bag covers are provided with releaseable fasteners at the top end to enable the ostomy bag to be removed from the cover for emptying or replacement. Again, the bag must be completely removed from the body for emptying which results in the same type of problems noted above.

Thus, it would be desirable to provide a cover for an ostomy bag which overcomes the problem associated with previously devised ostomy bag covers. It would also be desirable to provide an ostomy bag cover which completely encloses the ostomy bag to hide the contents within the bag from view. It would also be desirable to provide an ostomy bag cover which enables the ostomy bag to be emptied without requiring its removal from the body of the wearer. Finally, it would be desirable to provide an ostomy bag cover which is formed of a material which prevents irritation and discomfort when worn.

SUMMARY OF THE INVENTION

There is disclosed herein a new and improved cover for an ostomy bag of the type having an inlet, means for connecting the inlet in communication with a stoma on a body and a closeable outlet located at the bottom of the ostomy bag for emptying the contents therefrom. The cover is in the form of a hollow body and has a first aperture formed therein which is adapted to be disposed in registry with the inlet of the ostomy bag and to receive the connecting means therethrough. A second aperture is formed in the hollow body at a bottom portion thereof in proximity with the outlet of the ostomy bag so as to receive the outlet of the ostomy bag therethrough. Means, associated with the second aperture, are provided for releaseably closing the second aperture in the hollow body.

Preferably, the hollow body is formed of a soft fabric, such as cotton, so as to provide a comfortable feel to the wearer and to prevent the plastic ostomy bag from sticking to the skin of the wearer.

In a preferred embodiment, the second aperture is in the form of a narrow slot having spaced sides. Fastening means are applied to the spaced sides for releaseably closing the second aperture. Preferably a Velcro type fastener forms the fastening means of the present invention.

The ostomy bag cover of the present invention overcomes many of the problems associated with previsouly devised ostomy bag covers and affords several advantages when used. For one, the cover is formed of a soft fabric which provides comfort to the wearer when worn. The soft fabric also prevents the ostomy bag from sticking to and irritating the skin of the wearer.

Also, the cover is uniquely provided with a bottom located, closeable aperture which enables the contents of the ostomy bag to be emptied without requiring the ostomy bag to be removed from the body of the wearer. This not only minimizes the amount of time required to perform this rather unpleasant task but, also, significantly reduces skin irritation which is caused by frequent removal and re-attachment of the ostomy bag on the stoma.

BRIEF DESCRIPTION OF THE DRAWING

The various features, advantages and other uses of the present invention will become more apparent by the following detailed description and drawing in which:

FIG. 1 is a front elevational view of an ostomy bag cover constructed in accordance with the teachings of the present invention;

FIG. 2 is a partially exploded, front elevational view of a conventional ostomy bag adapted to be inserted in the cover illustrated in FIG. 1;

FIG. 3 is a cross-sectional view, generally taken along line 3—3 in FIG. 1, and

FIG. 4 is a side, cross-sectional view showing an ostomy bag mounted within the cover of the present invention.

DESCRIPTION OF THE PREFERRED EMBODIMENT

Throughout the following description and drawing, an identical reference number is used to refer to the same component shown in multiple figures of the drawing.

Refer now to the drawing, and to FIGS. 1 and 2 in particular, there is illustrated a cover 10 which is adapted to surround and enclose an ostomy bag 12. The cover 10 functions to enclose the ostomy bag 12 and hide the contents therein, provide a comfortable feel on the body of the wearer when worn, and enables the ostomy bag 12 to be emptied without requiring its complete removal from the body of the wearer.

The ostomy bag 12 is conventional in construction and, as shown in FIGS. 2 and 4, comprises a hollow receptacle 14 having an enlarged upper portion 16 and a narrower, lower throat portion 18. The hollow receptacle 14 is formed of any suitable material, such as vinyl plastic, polyethylene, polypropylene, etc., which has the requisite strength to hold waste material therein and is also impervious to gas and liquid. Further, the hollow receptacle 14 is formed with relatively thin side walls so as to enable the receptacle 14 to conform to the shape of the wearer's body.

An inlet aperture 20 is formed on one side of the hollow receptacle 14, preferably in the upper portion of the enlarged section 16. A connecting means 22 is provided for connecting the inlet 20 in fluid flow communication with a stoma on the body of a wearer. As is typical, the connecting means 22 is in the form of a circular plastic ring 24 having a plurality of outwardly extending tabs 26 formed therein which are used to attach the ring 24 to a belt or a skin shield mounted about the stoma. The inner surface of the plastic ring 24 is attached to one side of the hollow receptacle 14 by suitable means, such as by heat bonding or adhesives. In this manner, the plastic ring 24 extends outwardly from one side of the hollow receptacle 14 for easy and quick attachment to the stoma.

The hollow receptacle 14 is also provided with an outlet aperture 28 which is preferably situated at the bottom end of the narrow throat section 18. Preferably, the outlet 28 is in the form of a slot. As shown by the phantom lines in FIG. 2, the narrow throat portion 18 of the hollow receptacle 14 is adapted to be folded over several times and secured in a folded up position as shown in FIG. 4 by a suitable fastening means or clip 30 which is disposed about the opposed sides of the folded up throat section 18. In this manner, the bottom end of the hollow receptacle 14 is closed to the flow of gas and/or liquids so as to retain the waste products flowing through the stoma within the interior of the hollow receptacle 14.

In addition, the clip 30 can be removed and the bottom end for throat portion 18 unfolded so as to empty the contents from the interior of the hollow receptacle 14.

Referring now to FIGS. 1, 3 and 4, there is illustrated a cover 10 in the form of a hollow body. Preferably, the hollow body is formed of first and second planar members 40 and 42 which are secured or fastened together along substantially the entire length of their respective peripheral edges. A discontinuity or unfastened portion is provided along the bottom edge of the planar members 40 and 42, the purpose of which will be described in greater detail hereafter.

The cover 10 is formed in substantially the same shape as the ostomy bag 12 and includes an enlarged upper portion 44 and a narrow, lower throat portion 46.

Preferably, the cover 10 is formed of a soft fabric, such as cotton, so as to provide a comfortable feel when worn and to prevent sticking of the cover 10 and/or ostomy bag 12 to the wearer's body. Furthermore, the material chosen to form the cover 10 should be opaque so as to hide the contents of the ostomy bag 12 contained within the cover 10.

As shown in FIGS. 1 and 4, a first aperture 48 is formed in one of the first and second planar members, such as planar member 40. The first aperture 48 is positioned so as to be adapted to be disposed in registry with the inlet aperture 20 in the ostomy bag 12 when the ostomy bag 12 is inserted within the cover 10. Furthermore, the first aperture 48 in the cover 10 is adapted to receive the connecting means 22 on the ostomy bag 12 therethrough.

A second aperture 50 is formed in the lower throat portion 46 of the cover 10 and is adapted to be disposed in registry with the outlet 28 of the ostomy bag 12 so as to receive the outlet 28 therethrough. Preferably, the second aperture 50 is formed by the discontinuity or unfastened portion of the bottom peripheral edges of the first and second planar members 40 and 42. In this manner, as shown in FIGS. 3 and 4, the second aperture 50 is formed between spaced sides 52 and 54 of the lower portions of the first and second planar members 40 and 42, respectively.

The cover 10 is further provided with means 56 for releaseably closing the second aperture 50. Preferably, the fastening means 56 is fastened to the sides 52 and 54 of the first and second planar members 40 and 42. Although any type of fastening means 56 may be utilized to close the second aperture 50, it is preferred that mating Velcro-type strips be utilized. Thus, the pile portion 58 of a Velcro-type fastener is disposed and mounted on side 52; while the mating hook portion of a Velcor-type fastener is mounted on the opposed side 54.

In use, the ostomy bag 12 is inserted within the cover 10 through either of the first or second apertures 48 and 50. The connecting means 22 on the ostomy bag 12 is pulled through the first aperture 48 in the cover 10. The throat portion 18 of the ostomy bag 12 may be pulled through the second aperture 50, folded up and secured in a folded position by means of the clip 30 to sealingly close the bottom end of the ostomy bag 12. The second aperture 50 on the cover 10 is then closed. Finally, the cover 10 with the ostomy bag 12 mounted therein is attached to the body of the wearer by securing the connecting means 22 to the stoma.

During subsequent use, if it is necessary to empty the contents of the ostomy bag 12, the second aperture 50 in the cover portion end and the lower throat portion 18 of the ostomy bag 12 is pulled therethrough, unclipped and unfolded so as to enable the contents within the ostomy bag 12 to be emptied. It should be noted that during this emptying process, th ostomy bag 12 remains attached to the wearer. The bottom end of the ostomy bag 10 may then be reclosed for subsequent use after the lower throat portion 18 has been refolded. Conversely, the cover 10 and ostomy bag 12 may be removed from the wearer and the ostomy bag 12 removed from the cover 10 for cleaning or replacement if necessary.

Thus, there is been disclosed a new and improved cover for an ostomy bag which provides several distinct advantages over previously devised ostomy bag covers. For one, the cover is formed of a soft fabric which provides comfort when worn and prevents the ostomy bag from sticking to the body of the wearer. In addition, the cover is provided with a bottom releaseable aperture which enables the lower outlet of the ostomy bag to be emptied without requiring the ostomy bag to be removed from the patient, thereby avoiding unnecessary skin irritation and discomfort.

What is claimed is:

1. A combination cover and ostomy bag of the type having an inlet, means for connecting the inlet in communication with a stoma on a body and a closeable outlet located at the bottom of the ostomy bag for emptying the contents therefrom, the combination comprising:
   a ostomy bag;
   a hollow body;
   a first aperture formed in the hollow body and adapted to be disposed in registry with the inlet of the ostomy bag and to receive the connecting means therethrough;
   a second aperture means formed in the lower portion of the hollow body, the second aperture means disposed in proximity with the outlet of the ostomy bag so as to foldably receive the outlet of the ostomy bag therethrough; and
   means for releasable closing the second aperture in the hollow body to enable the oulet of the ostomy bag to be stored within the hollow body and passed through the second aperture to empty the contents of the ostomy bag therefrom.

2. The cover of claim 1 wherein the cover is formed of soft fabric material.

3. The cover of claim 1 wherein the closing means comprises a Velcro-type fastener.

4. The cover of claim 3 wherein the fabric material is cotton.

5. The cover of claim 1 wherein the hollow body comprises:
   first and second planar members;
   the first and second planar members being fastened together along substantially the entire length of the peripheral edges thereof; and
   the second aperture being formed between an unfastened portion of the peripheral edges of the first and second planar members.

6. A combination cover and ostomy bag of the type having an inlet means for connecting the inlet in communication with a stoma on a patient's body, a closeable outlet located at the bottom of the ostomy bag for emptying the contents therefrom and means for sealingly closing the outlet of the ostomy bag, the combination comprising:
   an ostomy bag;
   first and second planar members formed of a soft fabric material, the first and second planar members being fastened together along substantially the entire length of the peripheral edges thereof to define a hollow body;
   a first aperture formed in one of the first and second planar members and disposed in registry with the inlet of the ostomy bag and to receive the connecting means therethrough;
   a second aperture means formed in the bottom of the hollow body and defined by spaced, unfastened portions of the peripheral edges of the first and second planar members, the second aperture means disposed in proximity with the outlet of the ostomy bag so as to foldably receive the outlet therethrough; and
   means for releasably closing the second aperture means in the hollow body to enable the outlet of the ostomy bag to be stored within the hollow body and passed through the second aperture to empty the contents of the ostomy bag therefrom.

* * * * *